United States Patent [19]

Imai et al.

[11] Patent Number: 4,868,216

[45] Date of Patent: Sep. 19, 1989

[54] SULFAMOYL-SUBSTITUTED PHENETHYLAMINE DERIVATIVES AND PROCESS OF PRODUCING THEM

[75] Inventors: Kazuo Imai; Kunihiro Niigata; Takashi Fujikura, all of Saitama; Shinichi Hashimoto, Chiba; Toichi Takenaka, Tokyo, all of Japan

[73] Assignee: Yamanouchi Pharmaceutical Co., Ltd., Tokyo, Japan

[21] Appl. No.: 311,366

[22] Filed: Feb. 14, 1989

Related U.S. Application Data

[60] Continuation of Ser. No. 864,431, May 16, 1986, abandoned, which is a division of Ser. No. 756,790, Jul. 18, 1985, Pat. No. 4,703,063, which is a continuation of Ser. No. 632,258, Jul. 18, 1984, Pat. No. 4,558,156, which is a continuation of Ser. No. 403,006, Jul. 29, 1982, abandoned, which is a division of Ser. No. 231,421, Feb. 4, 1981, Pat. No. 4,373,106.

[30] Foreign Application Priority Data

Feb. 8, 1980 [JP] Japan .................................. 55-14382

[51] Int. Cl.$^4$ ............................................. A61K 31/18
[52] U.S. Cl. .................................................... 514/603
[58] Field of Search ........................................... 514/603

[56] References Cited

U.S. PATENT DOCUMENTS

| | | | |
|---|---|---|---|
| 3,723,524 | 3/1973 | Augatein et al. | 564/86 |
| 3,860,647 | 1/1975 | Colelle et al. | 564/86 |
| 4,140,713 | 2/1979 | Oxford et al. | 564/86 |
| 4,217,305 | 8/1980 | Imai et al. | 564/86 |
| 4,373,106 | 2/1983 | Imai et al. | 564/86 |
| 4,558,106 | 12/1985 | Imai et al. | 564/864 |
| 4,703,063 | 10/1987 | Imai et al. | 514/603 |

FOREIGN PATENT DOCUMENTS

| | | | |
|---|---|---|---|
| 0034432 | 8/1981 | European Pat. Off. | 564/86 X |
| 0159757 | 10/1982 | Japan | 564/86 X |
| 0041860 | 3/1983 | Japan | 564/86 X |

*Primary Examiner*—Paul F. Shaver
*Attorney, Agent, or Firm*—Burgess, Ryan & Wayne

[57] ABSTRACT

Novel sulfamoyl-substituted phenethylamine derivatives which exhibit α-adrenergic blocking action and are useful as an antihypertensive agent and an agent for the treatment of congestive heart failure.

1 Claim, No Drawings

SULFAMOYL-SUBSTITUTED PHENETHYLAMINE DERIVATIVES AND PROCESS OF PRODUCING THEM

This application is a continuation of 864,431, filed 5/16/86, now abandoned, which is a divisional of U.S. 756,790 filed 7/18/85 now U.S. Pat. No. 4,703,063 which is a continuation of U.S. 632,258 filed 7/18/84 now U.S. Pat. No. 4,558,156 which was a continuation of U.S. 403,006 filed 7/29/82 now abandoned, which was a divisional of U.S. 231,421, filed 2/4/81 Now U.S. Pat. No. 4,373,106.

BACKGROUND OF THE INVENTION

1. Field of the Invention

This invention relates to novel sulfamoyl-substituted phenethylamine derivatives and the acid addition salts thereof, and more particularly, to novel sulfamoyl-substituted phenethylamine derivatives and the acid addition salts thereof which exhibit a strong $\alpha$-adrenergic blocking action and are useful as an antihypertensive agent and a treating agent for congestive heart failure. The invention is further concerned with the process of producing these derivatives and the acid addition salts thereof.

2. Description of the Prior Art

British Pat. No. 2,006,772 discloses a series of compounds exhibiting $\alpha$- and $\beta$-adrenergic blocking actions and also the patent discloses that the compound shown by the following formula exhibits strong $\alpha$- and $\beta$-adrenergic blocking actions

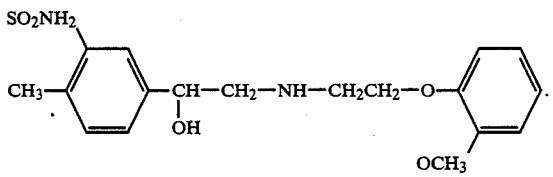

U.S. Pat. No. 3,860,647 discloses a series of compounds shown by the following general formula

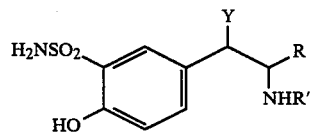

wherein R represents hydrogen or alkyl having 1-4 carbon atoms; R' represents alkyl having 1-6 carbon atoms, cycloalkyl having 3-6 carbon atoms, $XC_6H_4(CH_2)_2CH(CH_3)$, $XC_6H_4(CH_2)_2C(CH_3)_2$, $XC_6H_4CH_2CH(CH_3)$, or $XC_6H_4CH_2C(CH_3)_2$ (wherein X represents hydrogen, hydroxyl or methoxy); and Y represents hydrogen or hydroxy.

It is also described in the patent specification that these compounds exhibit a $\beta$-adrenergic blocking action.

British Pat. No. 902,617 discloses a series of compounds shown by the following general formula

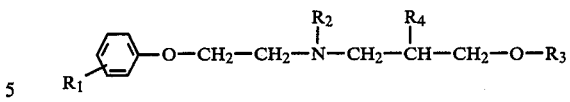

wherein $R_1$ is hydroxyl, methyl, methoxy, etc.; $R_2$ is hydrogen, methyl, etc.; $R_3$ is phenyl, benzyl or hydroxy-, methyl-, methoxy-, ethoxy-, chloro- or bromo-substituted phenyl or benzyl radical, etc.; and $R_4$ is hydrogen, etc. These compounds exhibit an $\alpha$-adrenergic blocking action (see, "J. Med. Chem."; 9, 812–818(1966)) and possess an antihypertensive activity.

Also, in "J. Med. Chem."; 9, 812–818(1966), there is described that the phenoxyethylamine-type compounds shown by the following general formula possess an $\alpha$-adrenergic blocking action;

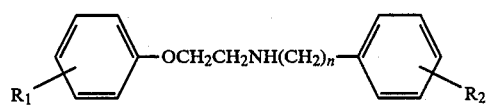

wherein $R_1$ represents o-OCH$_3$, etc., and $R_2$ represents o- or p-OCH$_3$, etc.

SUMMARY OF THE INVENTION

An object of this invention is to provide the novel sulfamoyl-substituted phenethylamine derivatives shown by following general formula and the acid addition salts thereof which possess a hypotensive activity based on an $\alpha$-adrenergic blocking action and are useful as an antihypertensive agent, an agent for the treatment of congestive heart failure, etc.

Another object of this invention is to provide the process for producing the above-described pharmaceutically useful compounds.

That is, according to this invention, there are provided the sulfamoyl-substituted phenethylamine derivatives shown by following general formula I and the acid addition salts thereof

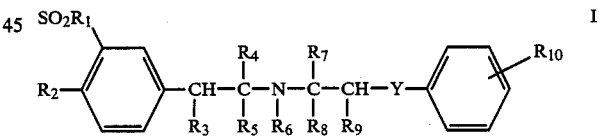

wherein $R_1$ represents, an amino group or a mono- or di-lower alkylamino group; $R_2$ represents, a hydroxyl group, a lower alkyl group, or a lower alkoxy group; $R_3$ represents, hydrogen atom, halogen atom, a lower alkyl group, a lower alkoxy group, a phenylthio group, or a phenylsulfinyl group; $R_4$, $R_5$, $R_6$, $R_7$, $R_8$ and $R_9$ each represents, hydrogen atom or a lower alkyl group; $R_{10}$ represents, hydrogen atom, a lower alkyl group, or a lower alkoxy group; and Y represents oxygen atom or a methylene group; said Y being, however, an oxygen atom when $R_2$ is a hydroxyl group.

DESCRIPTION OF THE PREFERRED EMBODIMENTS

Now, the term "lower" used in the above-described formula means a straight or branched carbon chain having 1 to 5 carbon atoms. Therefore, for example, a lower alkyl group includes a methyl group, ethyl group, propyl group, butyl group, pentyl group, isobutyl group, etc., and a lower alkoxy group includes a methoxy group, ethoxy group, propoxy group, butoxy group, etc. Also, in the above-described formula, $R_{10}$ which is a substituent of the benzene ring may be disposed at any position of which is ortho, meta or para to the side chain. Furthermore, since the compounds of this invention shown by formula I can readily form the salts thereof and contain asymmetric carbon atom(s), the compounds of this invention include the salts thereof, the racemic compounds thereof, a mixture of the racemic compounds, and each optically active substance.

The compounds of formula I and the acid addition salts thereof provided by the present invention exhibit an α-adrenergic blocking action and thus they can be utilized for various treatments. For example, they can be used as useful agents for the treatments of hypertension, congestive heart failure, angina pectoris, lower urinary tract dysfunction, prostatic hypertrophy, pheochromocytoma and peripheral vascular disorders.

The compounds of this invention shown by formula I can be produced by the following processes.

Process 1

The compounds of formula I are obtained by reacting the compounds shown by general formula II

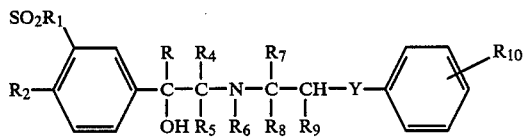

wherein R represents a hydrogen atom or a lower alkyl group and $R_1$, $R_2$, $R_4$, $R_5$, $R_6$, $R_7$, $R_8$, $R_9$, $R_{10}$ and Y have the same significance as in formula I with a halogenating agent and then, if desired, (a) reducing the halogenated product obtained by the above reaction; or (b) reacting the halogenated product with an alkaline material and then reacting the product thus obtained with hydrogen iodide, a lower alcohol, or thiophenol, and further, if desired, oxidizing the product obtained by the reaction with thiophenol.

Process 1 is further described in more detail. That is, according to the process, the starting materials shown by formula II described above are reacted with a halogenating agent to provide the compounds shown by general formula $I_1$

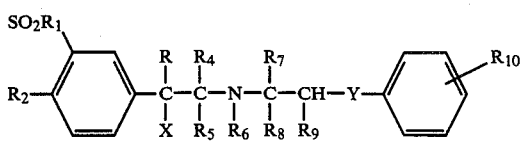

wherein X represents, chlorine atom or bromine atom and R, $R_1$, $R_2$, $R_4$, $R_5$, $R_6$, $R_7$, $R_8$, $R_9$, $R_{10}$ and Y have the same significance as in formula II and then, if desired, (a) the halogenated compounds shown by formula $I_1$ are reduced to form the compounds shown by formula $I_2$

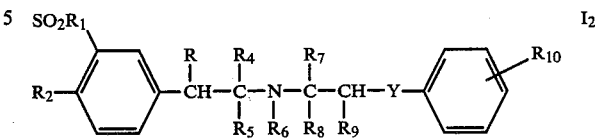

wherein R, $R_1$, $R_2$, $R_4$, $R_5$, $R_6$, $R_7$, $R_8$, $R_9$, $R_{10}$ and Y have the same significance as above described; or (b) the halogenated compounds shown by formula $I_1$ are treated with an alkaline material to form the aziridine compounds shown by the following general formula III

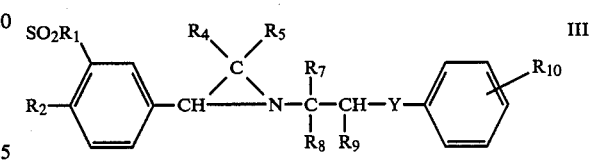

wherein $R_1$, $R_2$, $R_4$, $R_5$, $R_7$, $R_8$, $R_9$, $R_{10}$ and Y have the same significance as above described, then, the aziridine compounds are reacted with hydrogen iodide, a lower alcohol, or thiophenol to provide the compounds shown by general formula $I_3$

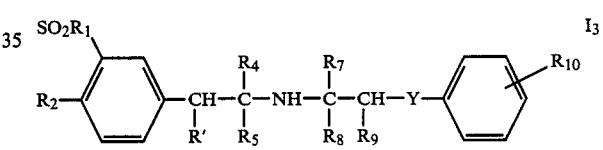

wherein R' represents an iodine atom, a lower alkoxy group or a phenylthio group and $R_1$, $R_2$, $R_4$, $R_5$, $R_7$, $R_8$, $R_9$, $R_{10}$ and Y have the same significance as above described and further, when R' of the compounds shown by formula $I_3$ is a phenylthio group, if desired, the compounds of $I_3$ are oxidized to provide the compounds shown by general formula $I_4$

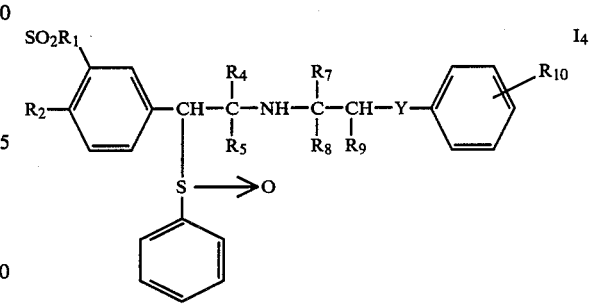

wherein $R_1$, $R_2$, $R_4$, $R_5$, $R_7$, $R_8$, $R_9$, $R_{10}$ and Y have the same significance as above described.

This process is further schematically shown below, wherein the compounds shown by formulae $I_1$, $I_2$, $I_3$ and $I_4$ are the desired compounds of this invention.

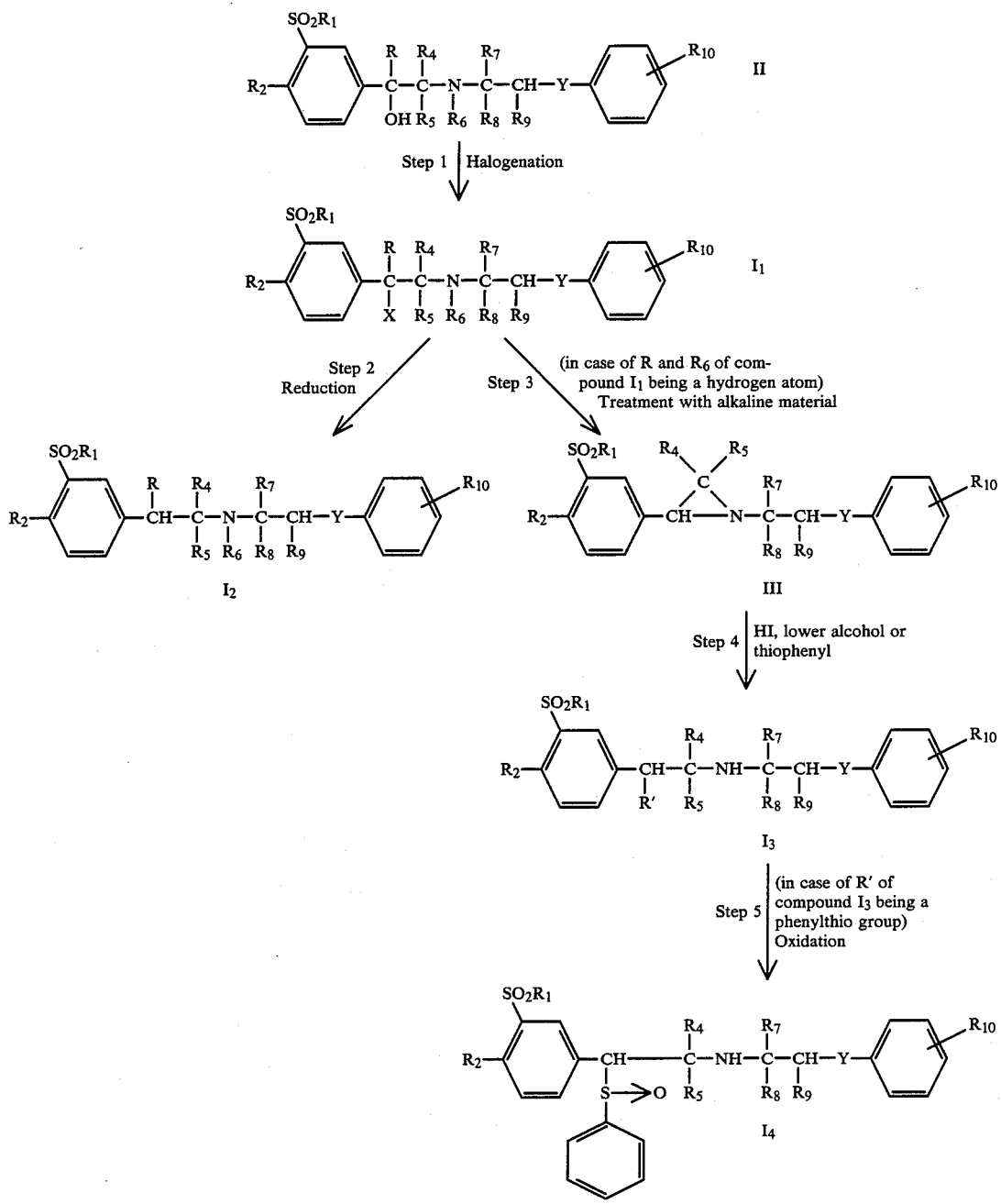

The reaction condition in each step described above is as follows:

Step 1:
The halogenation of the compounds of formula II can be performed in an organic solvent such as toluene, methyl ethyl ketone, acetonitrile, tetrahydrofuran, etc., at room temperature or under heating using a halogenating agent such as thionyl chloride, hydrogen chloride, hydrogen bromide, phosphorus trichloride, phosphorus pentachloride, phosphorus oxychloride, thionyl bromide, etc.

Step 2:
The reduction of the compounds of formula $I_1$ can be performed in an organic solvent such as methanol, ethanol, toluene, acetonitrile, tetrahydrofuran, etc., under a hydrogen stream, at normal temperature and normal pressure using a catalyst such as platinum oxide, palladium carbon, etc.

Step 3:
The compounds of formula III can be obtained by treating the compounds of formula $I_1$ (wherein, however, R and $R_6$ are hydrogen atom) with an alkaline material such as sodium carbonate, metal alcoholate, sodium hydroxide, potassium hydroxide, etc., in an organic solvent such as ethyl acetate, ethanol, dioxane, benzene, etc., at room temperature to 50° C.

Step 4:
(i):
The compounds of formula $I_3$ (wherein, R' is a phenylthio group) can be obtained by reacting the compounds of formula III with thiophenol in an organic solvent such as methanol, chloroform, ethyl acetate, dioxane, benzene, etc., at room temperature.

(ii):

The compounds of formula I₃ (wherein, R' is a lower alkoxy group) can be obtained by reacting the compounds of formula III with a lower alcohol in the presence of a BF₃ catalyst under the same condition as in the step i).

(iii):

The compounds of formula I₃ (wherein, R' is an iodine atom) can be obtained by reacting the compounds of formula III with hydroiodic acid in an organic solvent such as dioxane, methanol, etc., at room temperature.

Step 5:

The oxidation of the compounds of formula I₃ (wherein R' is a phenylthio group) can be performed in acetic acid at a temperature of 50°-60° C. using H₂O₂ as the oxidizing agent.

In addition, among the compounds of this invention, the compounds shown by following general formula I₅

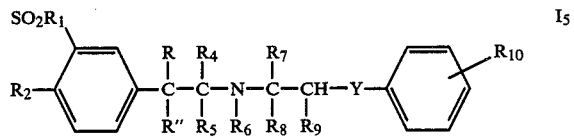

wherein R'' represents a lower alkoxy group or a phenylthio group and R, R₁, R₂, R₄, R₅, R₆, R₇, R₈, R₉, R₁₀ and Y have the same significance as above described can be obtained by reacting the compounds of formula I₁ directly with a lower alcohol or thiophenol.

The starting materials of formula II (wherein R is hydrogen atom) used in the process of this invention are described in British Pat. No. 2,006,772 and also the starting materials of formula II (wherein R is a lower alkyl group) can be obtained by reacting the compounds of the following formula

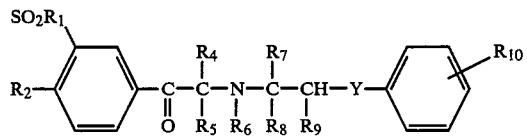

described in the aforesaid British patent with a Grignard reagent (lower alkyl-MgX).

Process 2

Among the compounds of formula I, the compounds of this invention shown by following general formula I₆

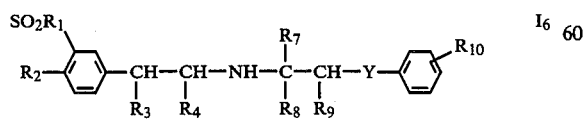

wherein R₁, R₂, R₃, R₄, R₇, R₈, R₉, R₁₀ and Y have the same significance as in formula I can be produced by condensing the compound shown by the general formula

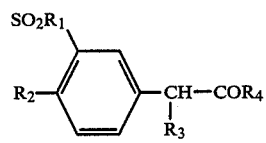

and the compound shown by the following formula

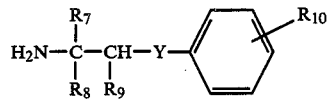

and then reducing the products thus obtained.

This reaction is performed by condensing the compounds of formula IV and the compounds of formula V in an organic solvent such as methanol, ethanol, toluene, acetonitrile, tetrahydrofuran, etc., and then reducing the products in the presence of a PtO₂ catalyst or a Raney nickel catalyst or with NaBH₄, LiAlH₄, etc.

The isolation and purification of the compounds of this invention shown by general formulae I₁-I₆ formed by Process 1 and 2 are performed by filtration, extraction with a solvent, separation by column chromatography, recrystallization, etc.

The pharmacological effects of the compounds of this invention were determined by the following experiments. The effects of the typical compounds of this invention were compared with 5-{1-hydroxy-2-[2-(2-methoxyphenoxy)ethylamino]ethyl}-2-methylbenzenesulfonamide (Compound A) which is one of the typical compounds disclosed in British Pat. No. 2,006,772 and phentolamine.

A. α-Adrenergic blocking action

The blood pressure was measured in the rats anesthetized with urethane and treated with pentolinium. The effects of the test samples (intravenous injection) to antagonize the hypertensive response to phenylephrine (10 μg/Kg i.v.) were measured and the results were shown in Table I.

B. Antihypertensive effects in spontaneously hypertensive rats

Oral administration: The systolic blood pressure was measured indirectly from the tail cuff method using a programmed electrosphygmanometer (Narco Bio-Systems Inc., PE-300) on spontaneously hypertensive rats having a systolic blood pressure higher than 150 mmHg, the results being shown in Table II.

TABLE I

| αAdrenergic blocking action: | |
|---|---|
| Sample Compounds of this inventioin (Ex. No.) | αadrenergic blocking ED₅₀ (mg/Kg) i.v. |
| 4 | 0.00035 |
| 5 | 0.00026 |
| 10 | 0.0059 |
| 11 | 0.012 |
| 12 | 0.0073 |
| 15 | 0.0013 |
| 16 | 0.0008 |
| 20 | 0.00000014 |
| 25 | 0.0012 |
| 26 | 0.004 |
| Known compounds | |
| Compound A | 0.034 |
| Phentolamine | 0.061 |

TABLE II

| | Antihypertensive effect: | |
|---|---|---|
| Sample Compounds of this invention (Ex. No.) | Dose (mg/Kg) | Change in systolic blood pressure (mmHg) at stated dose p.o. |
| 10 | 10 | −57 ± 5.6 |
| 11 | 30 | −50 ± 4.7 |
| 12 | 10 | −48 ± 2.0 |
| 15 | 10 | −54 ± 6.2 |
| 16 | 10 | −71 ± 11.1 |
| 20 | 3 | −57 ± 4.2 |
| 25 | 10 | −46 ± 3.6 |
| 26 | 10 | −46 ± 4.3 |
| Known compounds | | |
| Compound A | 10 | −35 ± 6.4 |
| Phentolamine | 10 | +7.8 ± 5.0 |
| " | 100 | −70 ± 10.1 |

The clinical administration of the compounds of this invention is usually practiced by intravenous injection or orally as the free bases or the acid addition salts thereof (e.g., hydrochlorides, sulfates, maleates, acetates, furarates, lactates, citrates, etc.). It is proper to administer 10 ng–1 mg per ounce of the compound several times per day in case of intravenous administration or 0.1–100 mg of the compound two or three times per day in the case of oral administration.

The compounds of this invention may be formulated into ordinary dosage forms such as, for example, tablets, capsules, pills, solutions, etc., and in these cases, the medicaments can be prepared by conventional methods with conventional pharmaceutical excipients.

Then, the production of the compounds of this invention will be further described in the following examples. In addition, the starting materials used in this invention include novel compounds and the production thereof are shown in the Reference Examples.

Reference Example 1

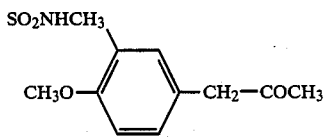

(1) To 250 g of chlorosulfonic acid was added dropwise 50 g of 4-methoxyphenylacetone at 0°–5° C. After stirring the mixture for 4 hours at room temperature, the reaction mixture was poured into 2,500 ml of ice water and extracted three with 500 ml of ethyl acetate. The extract was washed with water and after drying the extract with anhydrous magnesium sulfate, the solvent was distilled off under reduced pressure. The crude crystals obtained were recrystallized from benzene-ether to provide 32 g of 3-chlorosulfonyl-4-methoxyphenylacetone.

Melting point: 80°–81° C.

(2) In 26 ml of tetrahydrofuran was dissolved 2.6 g of 3-chlorosulfonyl-4-metnoxyphenylacetone and then 1.2 g of 40% methylamine was added dropwise to the solution at a temperature lower than 10° C. After stirring the mixture for one hour at room temperature, the solvent was distilled off under reduced pressure and the residue was extracted with ethyl acetate. The extract was washed with water and after drying with anhydrous magnesium sulfate, the solvent was distilled off under reduced pressure. The crude crystals obtained were recrystallized from isopropanol-ether to provide 1.8 g of 4-methoxy-3-N-methylsulfamylphenylacetone.

Melting point: 100°–101° C.

Reference Example 2

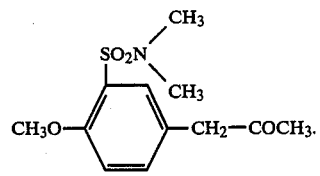

By reacting 2.6 g of 3-chlorosulfonyl-4-methoxyphenylacetone and 0.6 g of dimethylamine in the same manner as in Reference Example 1-(2), 2.5 g of oily 4-methoxy-3-N,N-dimethylsulfamylphenylacetone was obtained.

Nuclear magnetic resonance spectra (CDCl$_3$):
δ: 2.18 (3H, S, COCH$_3$)
2.82 (6H, S, N(CH$_3$)$_2$)
3.69 (2H, S,

| δ: | 2.18 (3H, s, COC$\underline{H_3}$) |
|---|---|
| | 2.82 (6H, S, N(C$\underline{H_3}$)$_2$) |
| | 3.69 (2H, S, 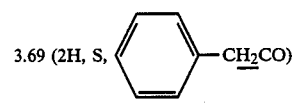—C$\underline{H_2}$CO) |
| | 3.90 (3H, S, O—C$\underline{H_3}$) |

3.90 (3H, S, O—CH$_3$)

EXAMPLE 1

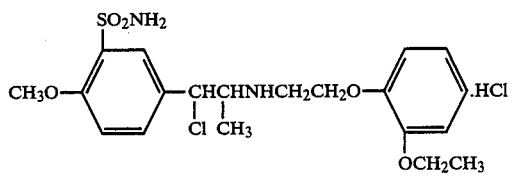

In 1,000 ml of acetonitrile was suspended 17 g of 5-{2-[2-(2-ethoxyphenoxy)ethylamino]-1-hydroxy-2-methyl-ethyl}-2-methoxybenzenesulfonamide hydrochloride and while stirring the suspension, 9 g of thionyl chloride was added dropwise to the suspension at room temperature, whereby the product was dissolved and then began to crystallize gradually. After stirring the mixture for two days, the crystals formed were recovered by filtration, washed with chloroform and dried to provide 15 g of 5-{1-chloro-2-[2-(2-ethoxyphenoxy)ethylamino]-2-methylethyl}-2-methoxybenzenesulfonamide hydrochloride.

The product has the following physicochemical properties.

Melting point: 197°–200° C.

Elemental analysis for C$_{20}$H$_{27}$N$_2$O$_5$SCl.HCl:

| | C(%) | H(%) | N(%) |
|---|---|---|---|
| Calcd. | 50.11 | 5.89 | 5.84 |

-continued

|  | C(%) | H(%) | N(%) |
|---|---|---|---|
| Found | 50.06 | 5.96 | 5.95 |

Nuclear magnetic resonance spectra (CD$_3$OD):

δ:  1.30 (3H, d, CH—C$\underline{H}_3$)

1.40 (3H, t, CH$_2$—C$\underline{H}_3$)

3.63 (2H, t, CH$_2$—C$\underline{H}_2$—N)

4.01 (3H, s, O—C$\underline{H}_3$)

4.12 (2H, q, CH$_3$—C$\underline{H}_2$—O)

4.36 (2H, t, CH$_2$—C$\underline{H}_2$—O)

5.30 (1H, d, Cl—C$\underline{H}$)

The compounds in Examples 2 and 3 were obtained in the same manner as in Example 1.

EXAMPLE 2

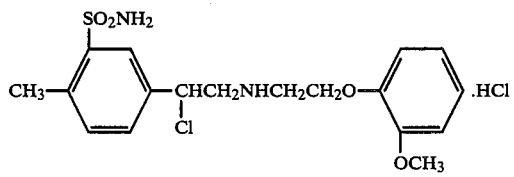

5-{1-Chloro-2-[2-(2-methoxyphenoxy)ethylamino]ethyl}-2-methylbenzenesulfonamide hydrochloride Physicochemical properties Melting point: 190°–191° C.

Elemental analysis for C$_{18}$H$_{23}$N$_2$O$_4$SCl.HCl:

|  | C(%) | H(%) | N(%) |
|---|---|---|---|
| Calculated | 49.66 | 5.56 | 6.43 |
| Found | 49.51 | 5.70 | 6.53 |

Nuclear magnetic resonance spectra (d$_6$-DMSO)

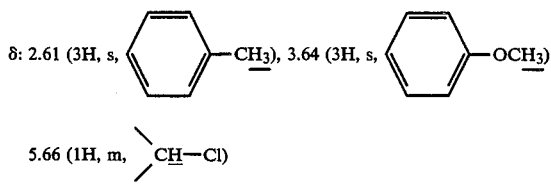

EXAMPLE 3

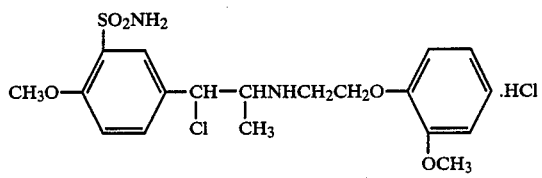

5-{1-Chloro-2-[2-(2-methoxyphenoxy)ethylamino]-2-methylethyl}-2-methoxybenzenesulfonamide hydrochloride Physicochemical properties Melting point: 195°–197° C. (decomposed)

Elemental analysis for C$_{19}$H$_{25}$N$_2$O$_5$SCl.HCl:

|  | C(%) | H(%) | N(%) |
|---|---|---|---|
| Calculated | 49.04 | 5.63 | 6.02 |
| Found | 49.02 | 5.64 | 6.08 |

Nuclear magnetic resonance spectra (CD$_3$OD+d$_6$-DMSO)

δ: 1.18 (3H, d,

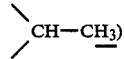

3.80 and 3.95 (3H+3H, s, —O—CH$_3$)

5.56 (1H, d,

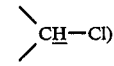

EXAMPLE 4

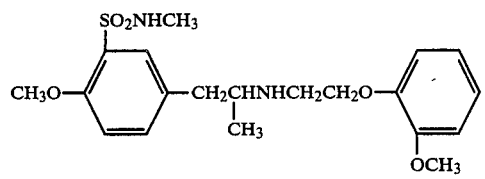

A mixture of 1.4 g of 4-methoxy-3-N-methylsulfamylphenylacetone, 1 g of 2-methoxyphenoxyethylamine, and 30 ml of methanol was refluxed for one hour. After cooling the mixture, 60 mg of a platinum oxide catalyst was added thereto, the reduction was performed at normal temperature and pressure. After absorbing a theoretical amount of hydrogen, the catalyst was filtered away. After the filtrate was acidified with an alcoholic 5% hydrochloric acid, the solvent was distilled off under reduced pressure to form 1.6 g of crystals, which were recovered and recrystallized to provide 1.2 g of the colorless crystals of 2-methoxy-5-{2-[2-(2-methoxyphenoxy)ethylamino]-2-methylethyl}-N-methylbenzenesulfonamide hydrochloride.

The product has the following physicochemical properties.

Melting point: 162°–163° C.

Elemental analysis for $C_{20}H_{28}N_2O_5S \cdot HCl$:

|  | C(%) | H(%) | N(%) |
|---|---|---|---|
| Calcd. | 53.99 | 6.57 | 6.30 |
| Found | 53.85 | 6.70 | 6.27 |

Nuclear magnetic resonance spectra ($d_6$-DMSO)
δ: 1.15 (3H, d, —CHCH$_3$)
3.76 and 3.88 (3H+3H, S, O—CH$_3$)
The product of Example 5 was obtained in the same manner as in Example 4.

EXAMPLE 5

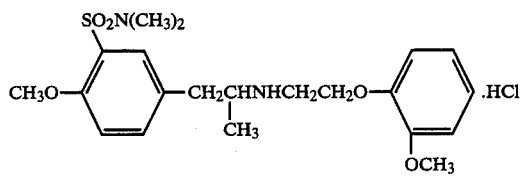

2-Methoxy-5-{2-[2-(2-methoxyphenoxy)ethylamino]-2-methylethyl}-N,N-dimethylbenzenesulfonamide hydrochloride
Physicochemical properties
Melting point: 185°–187° C.
Elemental analysis for $C_{21}H_{30}N_2O_5S \cdot HCl$

|  | C(%) | H(%) | N(%) |
|---|---|---|---|
| Calculated | 54.95 | 6.81 | 6.10 |
| Found | 54.73 | 6.88 | 5.85 |

Nuclear magnetic resonance spectra ($d_6$-DMSO)
δ: 1.16 (3H, d, CHOH$_3$), 2.71 (6H, s, N(CH$_3$)$_2$)
3.76 and 3.87 (3H+3H, s, —O—CH$_3$)

Reference Example 3

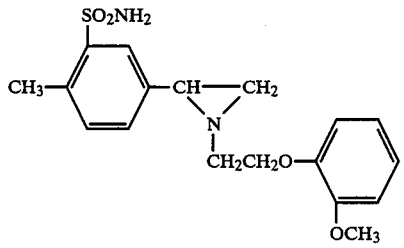

In 50 ml of ethyl acetate was suspended 4.35 g (0.01 mole) of 5-{1-chloro-2-[2-(2-methoxyphenoxy)ethylamino]ethyl}-2-methylbenzenesulfonamide hydrochloride and then 50 ml of an aqueous 10% sodium carbonate solution was added to the suspension with stirring. After further stirring overnight vigorously, the reaction mixture was recovered by decantation. After removing inorganic materials by passing the ethyl acetate layer thus recovered through a silica gel column (50 ml of silica gel), the reaction product was evaporated to dryness to provide 3.2 g (88%) of colorless resinous 5-{1-[2-(2-methoxyphenoxy)-ethyl]aziridin-2-yl}-2-methylbenzenesulfonamide. The product has the following physicochemical properties.
Amorphous form.
Elemental analysis for $C_{18}H_{22}N_2O_4S$:

|  | C(%) | H(%) | N(%) |
|---|---|---|---|
| Calcd. | 59.65 | 6.12 | 7.73 |
| Found | 59.37 | 6.12 | 7.61 |

Nuclear magnetic resonance spectra (CDCl$_3$):

| δ: | 1.74 and 1.95 | (1H + 1H, d, ) |
|---|---|---|
|  | 2.43 | (1H, q, H-C-CH2 / N) |
|  | 2.55 | (3H, s, C$_6$H$_4$—CH$_3$) |
|  | 4.10 | (2H, t, O—CH$_2$—) |

EXAMPLE 6

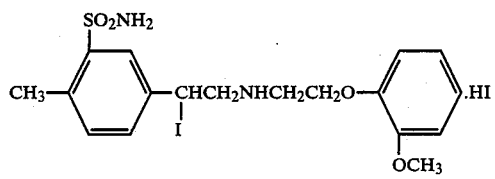

In 50 ml of dioxane was dissolved 2.5 g of 5-{1-[2-(2-methoxyphenoxy)ethyl]aziridin-2-yl}-2-methylbenzenesulfonamide and after adding thereto 1 g of concentrated hydroiodic acid, the mixture was stirred overnight. After the reaction was over, the solvent was distilled off under reduced pressure and the residue was washed three with 30 ml of water and then three with 200 ml of ether and crystallized by the addition of ethyl acetate. The crystals were recovered by filtration, washed with water, and dried to provide 1.7 g of 5-{1-iodo-2-[2-(2-methoxyphenoxy)ethylamino]ethyl}-2-methylbenzenesulfonamide hydroiodide. The product has the following physicochemical properties.
Melting point: 154°–155° C.
Elemental analysis for $C_{18}H_{23}N_2O_4SI \cdot HI$:

|  | C(%) | H(%) | N(%) |
|---|---|---|---|
| Calcd. | 34.97 | 3.91 | 4.53 |
| Found | 35.07 | 3.98 | 4.39 |

Nuclear magnetic resonance spectra (CD$_3$OD):

δ:
2.65 (3H, s, C$_6$H$_4$—CH$_3$)

3.54 (2H, t, —CH$_2$—N—)

4.30 (2H, t, —CH$_2$—O)

-continued 5.55 (1H, t, 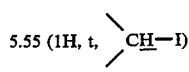)

EXAMPLE 7

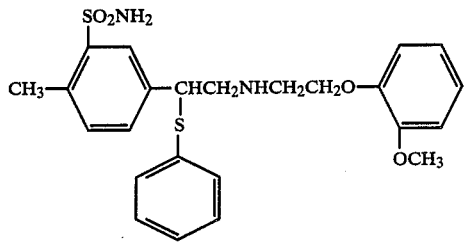

In 50 ml of methanol was dissolved 2.5 g of 5-{1-[2-(2-methoxyphenoxy)ethyl]aziridin-2-yl}-2-methylbenzenesulfonamide and after adding 1 g of thiophenol to the solution and stirring overnight the mixture at room temperature, methanol was distilled off. The residue was applied to a silica gel column chromatography and the product was eluted with a mixed solvent of chloroform and methanol (9:1 by volume ratio) to provide 2.4 g of 5-{2-[2-(2-methoxyphenoxy)-ethylamino]-1-phenylthioethyl}-2-methylbenzenesulfonamide as a viscous oily material.

The product has the following physicochemical properties.

Amorphous form.

Elemental analysis for $C_{24}H_{28}N_2O_4S_2$:

| | C(%) | H(%) | N(%) |
|---|---|---|---|
| Calcd. | 60.99 | 5.97 | 5.93 |
| Found | 60.72 | 6.11 | 5.71 |

Nuclear magnetic resonance spectra (CDCl₃):

δ:

2.58 (3H, s, 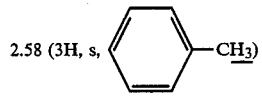)

3.74 (3H, s, O—CH₃)

3.98 (2H, t, —CH₂—O)

4.35 (1H, t, )

EXAMPLE 8

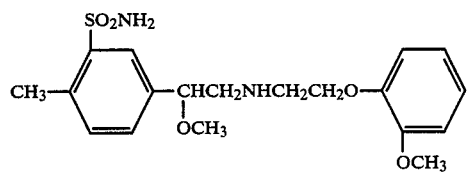

In 50 ml of methanol was dissolved 2.5 g of 5-{1-[2-(2-methoxyphenoxy)ethyl]aziridin-2-yl}-2-methylbenzenesulfonamide and after adding thereto 2 ml of a boron trifluoride ether complex at room temperature, the mixture was stirred overnight. Thereafter, methanol was distilled off under reduced pressure and the residue was applied to a silica gel column chromatography. The product was then eluted with a mixed solvent of chloroform and methanol (9:1 by volume ratio), whereby 1.5 g of a colorless viscous oily material was obtained. The product was crystallized by the addition of 5 ml of methanol and several drops of ammonia. The crystals formed were recovered by filtration, washed with water, and dried to provide 1.2 g of 5-{1-methoxy-2-[2-(2-methoxyphenoxy)ethylamino]ethyl}-2-methylbenzenesulfonamide.

The product has the following physicochemical properties.

Melting point: 150°–152° C.

Elemental analysis for $C_{19}H_{26}N_2O_5S$:

| | C(%) | H(%) | N(%) |
|---|---|---|---|
| Calcd. | 57.85 | 6.64 | 7.10 |
| Found | 57.58 | 6.79 | 7.24 |

Nuclear magnetic resonance spectra (CD₃OD):

δ:

2.65 (3H, s, 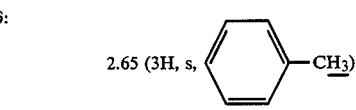)

2.98 (2H, t, —CH₂N)

3.80 (3H, s, 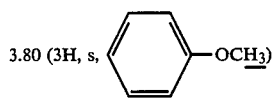)

3.26 (3H, s, CH—OCH₃)

4.10 (2H, t, —CH₂O)

4.40 (1H, q, )

EXAMPLE 9

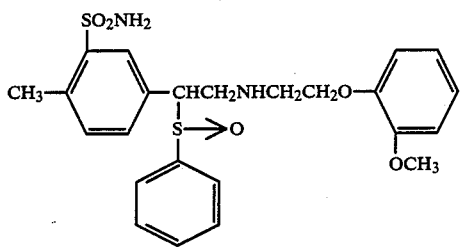

In 20 ml of acetic acid was dissolved 2 g of 5-{2-[2-(2-methoxyphenoxy)ethylamino]-1-phenylthioethyl}-2-methylbenzenesulfonamide and after adding thereto 0.5 ml of 30% $H_2O_2$, the mixture was heated to 50°–60° C. for 3 hours. After adding thereto 100 ml of water, the reaction mixture was extracted with 200 ml of ethyl acetate. The ethyl acetate extract was washed with an aqueous 1% sodium carbonate solution and then ethyl acetate was distilled off under reduced pressure. The residue was applied to a silica gel column chromatography, the product was eluted with a mixed solvent of chloroform and methanol (9:1 by volume ratio), and the colorless viscous oily product thus obtained was crystallized by the addition of ethyl acetate. The crystals formed were recovered by filtration to provide 1.3 g of 5-{2-[2-(2-methoxyphenoxy)-ethylamino]-1-phenylsulfinylethyl}-2-methylbenzenesulfonamide.

The product has the following physicochemical properties.
Melting point: 139°–141° C.
Elemental analysis for $C_{24}H_{28}N_2O_5S_2$:

|  | C(%) | H(%) | N(%) |
|---|---|---|---|
| Calcd. | 59.00 | 5.78 | 5.73 |
| Found | 58.91 | 5.74 | 5.72 |

EXAMPLE 10

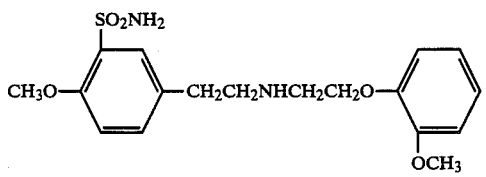

In 150 ml of methanol was dissolved 3.8 g of 5-{1-chloro-2-[2-(2-methoxyphenoxy)ethylamino]ethyl}-2-methoxybenzenesulfonamide hydrochloride and after adding thereto 0.5 g of 10% palladium carbon, it was dechlorinated under a hydrogen stream at normal temperature and pressure. Then, palladium carbon was filtered away and the filtrate was concentrated under reduced pressure to provide 3.1 g of 2-methoxy-5-{2-[2-(2-methoxyphenoxy)ethylamino]ethyl}benzene-sulfonamide hydrochloride, which was recrystallized from 120 ml of a mixture of methanol and ethanol (1:4 by volume ratio) to provide 2.3 g of the colorless crystals thereof.

The product has the following physicochemical properties.
Melting point: 196°–198° C.
Elemental analysis for $C_{18}H_{24}N_2O_5S.HCl$):

|  | C(%) | H(%) | N(%) |
|---|---|---|---|
| Calcd. | 51.86 | 6.04 | 6.72 |
| Found | 51.72 | 6.23 | 6.68 |

Nuclear magnetic resonance spectra (CD$_3$OD):
δ: 3.84 and 3.98 (3H+3H, s, —OCH$_3$)
4.24 (2H, t, —OCH$_2$—)

The compounds in Examples 11–29 were obtained in the same manner as in Example 10.

EXAMPLE 11

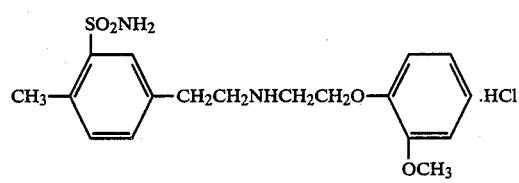

5-{2-[2-(2-Methoxyphenoxy)ethylamino]ethyl}-2-methylbenzenesulfonamide hydrochloride
Physicochemical properties
Melting point: 173°–175° C.
Elemental analysis for $C_{18}H_{24}N_2O_4S.HCl$:

|  | C(%) | H(%) | N(%) |
|---|---|---|---|
| Calculated | 53.93 | 6.28 | 6.99 |
| Found | 53.83 | 6.27 | 6.97 |

Nuclear magnetic resonance spectra (CD$_3$OD)

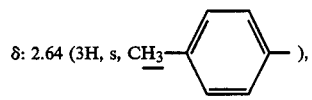

3.84 (3H, s, —OCH$_3$)
4.28 (2H, t, —OCH$_2$—)

EXAMPLE 12

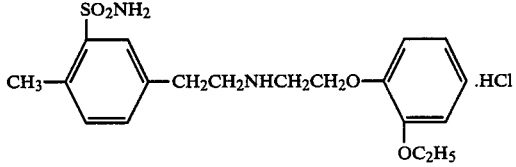

5-{2-[2-(2-Ethoxyphenoxy)ethylamino]ethyl}-2-methylbenzenesulfonamide hydrochloride
Physicochemical properties
Melting point: 180°–181.5° C.
Elemental analysis for $C_{19}H_{26}N_2O_4S.HCl$

|  | C(%) | H(%) | N(%) |
|---|---|---|---|
| Calculated | 55.00 | 6.56 | 6.75 |
| Found | 54.81 | 6.56 | 6.89 |

Nuclear magnetic resonance spectra (CD$_3$OD)

δ: 1.36 (3H, t, —OCH$_2$CH$_3$), 2.64 (3H, s, CH$_3$— 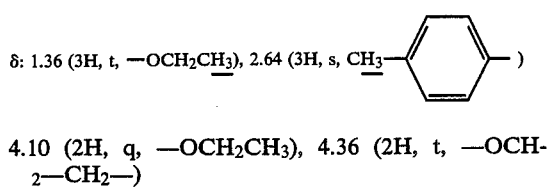)

4.10 (2H, q, —OCH$_2$CH$_3$), 4.36 (2H, t, —OCH$_2$—CH$_2$—)

EXAMPLE 13

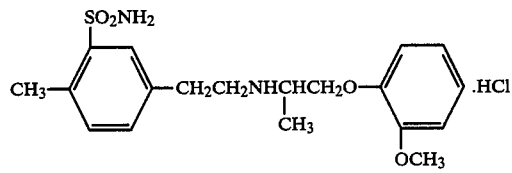

5-{2-[2-(2-Methoxyphenoxy)-1-methylethylamino]ethyl}-2-methylbenzenesulfonamide hydrochloride
Physicochemical properties
Melting point: 169°–171° C.
Elemental analysis for C$_{19}$H$_{26}$N$_2$O$_4$S.HCl

|  | C(%) | H(%) | N(%) |
|---|---|---|---|
| Calculated | 55.00 | 6.56 | 6.75 |
| Found | 54.89 | 6.60 | 6.76 |

Nuclear magnetic resonance spectra (CD$_3$OD)

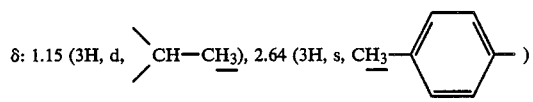

δ: 1.15 (3H, d, \CH—CH$_3$/), 2.64 (3H, s, CH$_3$— )

3.80 (3H, s, —OCH$_3$)

EXAMPLE 14

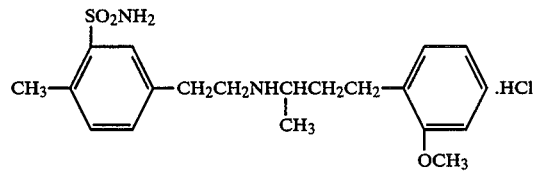

5-{2-[3-(2-Methoxyphenyl)-1-methylpropylamino]ethyl}-2-methylbenzenesulfonamide hydrochloride
Physicochemical properties
Melting point: 198°–200° C.
Elemental analysis for C$_{20}$H$_{28}$N$_2$O$_3$S.HCl

|  | C(%) | H(%) | N(%) |
|---|---|---|---|
| Calculated | 58.17 | 7.08 | 6.78 |
| Found | 58.09 | 7.01 | 6.62 |

Nuclear magnetic resonance spectra (d$_6$-DMSO)

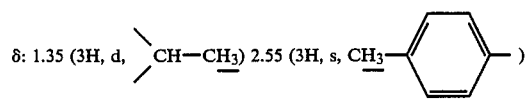

δ: 1.35 (3H, d, \CH—CH$_3$/) 2.55 (3H, s, CH$_3$— )

3.78 (3H, s, —OCH$_3$)

EXAMPLE 15

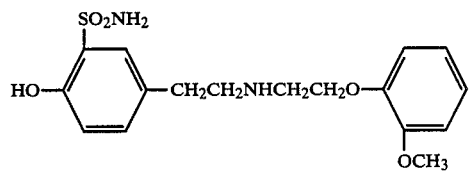

2-Hydroxy-5-{2-[2-(2-methoxyphenoxy)ethylamino]ethyl}benzenesulfonamide
Physicochemical properties
Melting point: 97°–99° C.
Elemental analysis for C$_{17}$H$_{22}$N$_2$O$_5$S.H$_2$O

|  | C(%) | H(%) | N(%) |
|---|---|---|---|
| Calculated | 53.10 | 6.29 | 7.29 |
| Found | 52.75 | 6.22 | 7.09 |

Nuclear magnetic resonance spectra (d$_6$-DMSO)
δ: 3.76 (3H, s, —OCH$_3$)
4.04 (2H, t, —OCH$_2$—)

EXAMPLE 16

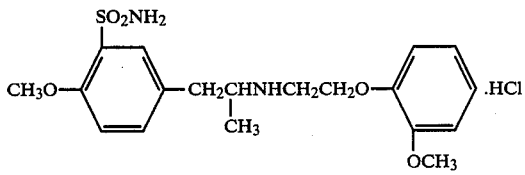

2-Methoxy-5-{2-[2-(2-methoxyphenoxy)ethylamino]-2-methylethyl}benzenesulfonamide hydrochloride
Physicochemical properties
Melting point: above 250° C.
Elemental analysis for C$_{19}$H$_{26}$N$_2$O$_5$S.HCl

|  | C(%) | H(%) | N(%) |
|---|---|---|---|
| Calculated | 52.96 | 6.31 | 6.50 |
| Found | 52.44 | 6.31 | 6.47 |

Nuclear magnetic resonance spectra (d$_6$-DMSO)
δ 1.15

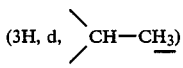

(3H, d, \CH—CH$_3$/)

3.78 and 3.90 (3H+3H, s, —OCH$_3$)
4.38 (2H, t, —OCH$_2$—)

EXAMPLE 17

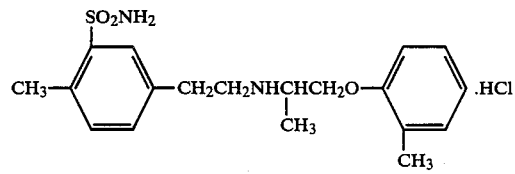

2-Methyl-5-{2-[2-(2-methylphenoxy)-1-methylethylamino]ethyl}benzenesulfonamide hydrochloride
Physicochemical properties
Melting point: 183°-185° C.
Elemental analysis for $C_{19}H_{26}N_2O_3S \cdot HCl$:

|  | C(%) | H(%) | N(%) |
|---|---|---|---|
| Calculated | 57.20 | 6.82 | 7.02 |
| Found | 57.13 | 6.79 | 6.99 |

Nuclear magnetic resonance spectra ($CD_3OD$)

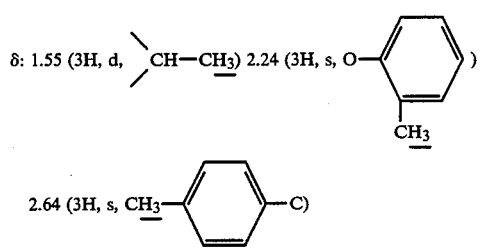

δ: 1.55 (3H, d, $\ce{>CH-CH3}$) 2.24 (3H, s, O—)

2.64 (3H, s, $CH_3$—)

2.08–2.40 (2H, m, —$OCH_2$—)

EXAMPLE 18

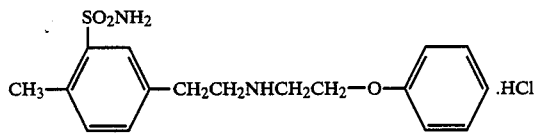

2-Methyl-5-[2-(2-phenoxyethylamino)ethyl]benzenesulfonamide hydrochloride
Physicochemical properties
Melting point: 208.5°–210° C.
Elemental analysis for $C_{17}H_{22}N_2O_3S \cdot HCl$:

|  | C(%) | H(%) | N(%) |
|---|---|---|---|
| Calculated | 55.05 | 6.25 | 7.55 |
| Found | 54.83 | 6.23 | 7.48 |

Nuclear magnetic resonance spectra ($CD_3OD$)

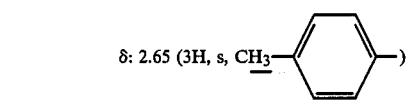

δ: 2.65 (3H, s, $CH_3$—)

4.32 (2H, t, —$OCH_2$)

EXAMPLE 19

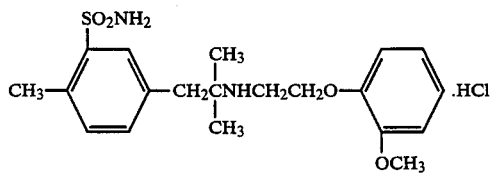

5-{2-[2-(2-Methoxyphenoxy)ethylamino]-2,2-dimethylethyl}-2-methylbenzenesulfonamide hydrochloride
Physicochemical properties
Melting point: 199°–202° C.

Elemental analysis for $C_{20}H_{28}N_2O_4S \cdot HCl \cdot CH_3OH$

|  | C(%) | H(%) | N(%) |
|---|---|---|---|
| Calculated | 54.71 | 7.21 | 6.08 |
| Found | 54.50 | 7.17 | 6.14 |

Nuclear magnetic resonance spectra ($d_6$-DMSO)

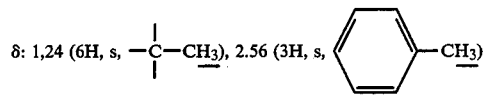

δ: 1.24 (6H, s, $\ce{-C(CH3)(CH3)-}$), 2.56 (3H, s, —$CH_3$)

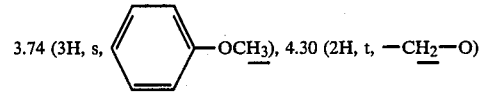

3.74 (3H, s, —$OCH_3$), 4.30 (2H, t, —$CH_2$—O)

EXAMPLE 20

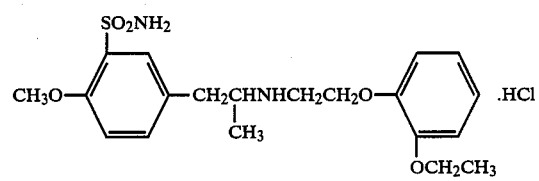

5-{2-[2-(2-Ethoxyphenoxy)ethylamino]-2-methylethyl}-2-methoxybenzenesulfonamide hydrochloride
Physicochemical properties
Melting point: 254°–256° C.
Elemental analysis for $C_{20}H_{28}N_2O_5S \cdot HCl$

|  | C(%) | H(%) | N(%) |
|---|---|---|---|
| Calculated | 53.99 | 6.57 | 6.30 |
| Found | 53.79 | 6.58 | 6.26 |

Nuclear magnetic resonance spectra ($CD_3OD$)
δ: 1.28

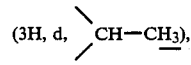

(3H, d, $\ce{>CH-CH3}$), 1.38 (3H, t, $CH_2$—$CH_3$)
3.97 (3H, s, O—$CH_3$), 4.30 (2H, t, $CH_2$—$CH_2$—O)

EXAMPLE 21

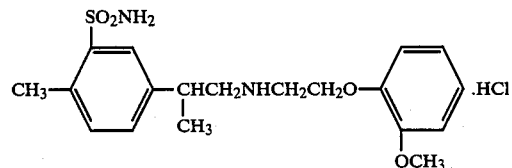

5-{2-[2-(2-Methoxyphenoxy)ethylamino]-1-methylethyl}-2-methylbenzenesulfonamide hydrochloride
Physicochemical properties
Melting point: 183°–185° C.
Elemental analysis for $C_{19}H_{26}N_2O_4S \cdot HCl$:

|            | C(%)  | H(%) | N(%) |
|------------|-------|------|------|
| Calculated | 55.00 | 6.56 | 6.75 |
| Found      | 54.76 | 6.56 | 6.74 |

Nuclear magnetic resonance spectra (CD$_3$OD)

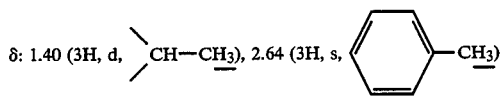
δ: 1.40 (3H, d, CH—C$\underline{H_3}$), 2.64 (3H, s, — C$\underline{H_3}$)

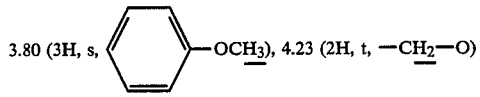
3.80 (3H, s, —OC$\underline{H_3}$), 4.23 (2H, t, —C$\underline{H_2}$—O)

EXAMPLE 22

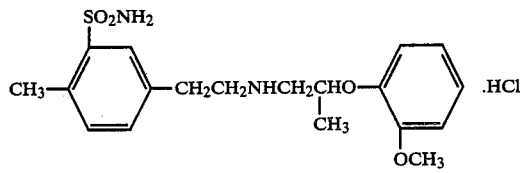

5-{2-[2-(2-Methoxyphenoxy)-2-methylethylamino]ethyl}-2-methylbenzenesulfonamide hydrochloride
Physicochemical properties
  Melting point: 231°–232° C.
  Elemental analysis for C$_{19}$H$_{26}$N$_2$O$_4$S.HCl:

|            | C(%)  | H(%) | N(%) |
|------------|-------|------|------|
| Calculated | 55.00 | 6.56 | 6.75 |
| Found      | 54.86 | 6.58 | 6.83 |

Nuclear magnetic resonance spectra (CD$_3$OD)

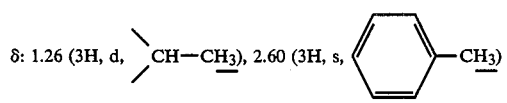
δ: 1.26 (3H, d, CH—C$\underline{H_3}$), 2.60 (3H, s, —C$\underline{H_3}$)

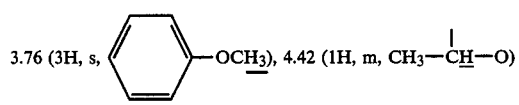
3.76 (3H, s, —OC$\underline{H_3}$), 4.42 (1H, m, CH$_3$—C$\underline{H}$—O)

EXAMPLE 23

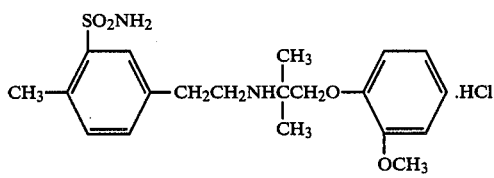

5-{2-[2-(2-Methoxyphenoxy)-1,1-dimethylethylamino]ethyl}-2-methylbenzenesulfonamide hydrochloride
Physicochemical properties
  Melting point: 191°–193° C.

Elemental analysis for C$_{20}$H$_{28}$N$_2$O$_4$S.HCl

|            | C(%)  | H(%) | N(%) |
|------------|-------|------|------|
| Calculated | 56.00 | 6.81 | 6.53 |
| Found      | 55.83 | 6.86 | 6.32 |

Nuclear magnetic resonance spectra (d$_6$-DMSO)

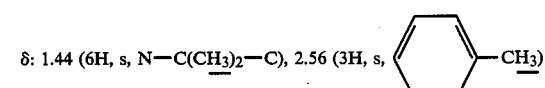
δ: 1.44 (6H, s, N—C(C$\underline{H_3}$)$_2$—C), 2.56 (3H, s, —C$\underline{H_3}$)

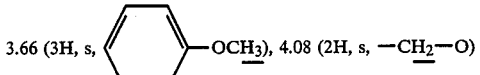
3.66 (3H, s, —OC$\underline{H_3}$), 4.08 (2H, s, —C$\underline{H_2}$—O)

EXAMPLE 24

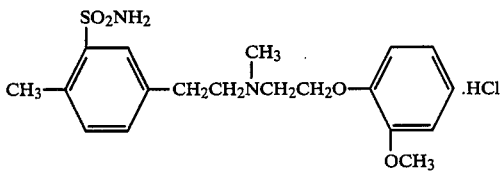

5-{2-[N-[2-(2-Methoxyphenoxy)ethyl]-N-methylamino]ethyl}-2-methylbenzenesulfonamide hydrochloride
Physicochemical properties
  Melting point: 169°–171° C.
  Elemental analysis for C$_{19}$H$_{26}$N$_2$O$_4$S.HCl:

|            | C(%)  | H(%) | N(%) |
|------------|-------|------|------|
| Calculated | 55.00 | 6.56 | 6.75 |
| Found      | 54.88 | 6.51 | 6.64 |

Nuclear magnetic resonance spectra (d$_6$-DMSD)

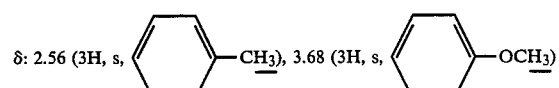
δ: 2.56 (3H, s, —C$\underline{H_3}$), 3.68 (3H, s, —OC$\underline{H_3}$)

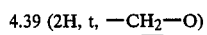
4.39 (2H, t, —C$\underline{H_2}$—O)

EXAMPLE 25

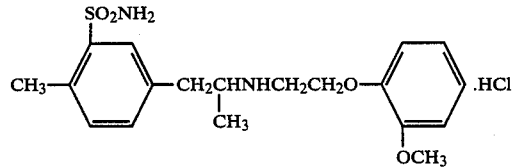

5-{2-[2-(2-Methoxyphenoxy)ethylamino]-2-methylethyl}-2-methylbenzenesulfonaimde hydrochloride
Physicochemical properties
  Melting point: 250°–252° C.
  Elemental analysis for C$_{19}$H$_{26}$N$_2$O$_4$S.HCl

|            | C(%)  | H(%) | N(%) |
|------------|-------|------|------|
| Calculated | 55.00 | 6.56 | 6.75 |
| Found      | 54.68 | 6.49 | 6.58 |

Nuclear magnetic resonance spectra (CDCl$_3$+d$_6$-DMSO+D$_2$O+Na$_2$CO$_3$)

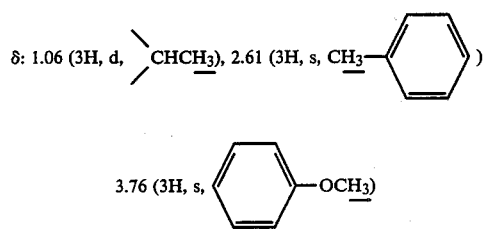

EXAMPLE 26

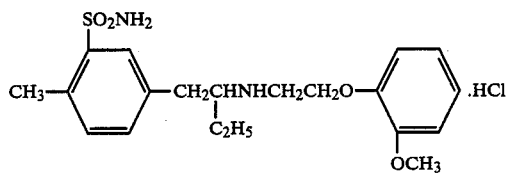

5-{2-[2-(2-Methoxyphenoxy)ethylamino]-2-ethylethyl}-2-methylbenzenesulfonamide hydrochloride
Physicochemical properties
 Melting point: 198°–200° C.
 Elemental analysis for C$_{20}$H$_{28}$N$_2$O$_4$S.HCl

|            | C(%)  | H(%) | N(%) |
|------------|-------|------|------|
| Calculated | 56.00 | 6.81 | 6.53 |
| Found      | 55.76 | 6.88 | 6.51 |

Nuclear magnetic resonance spectra (CDCl$_3$+d$_6$-DMSO+D$_2$O+Na$_2$CO$_3$)

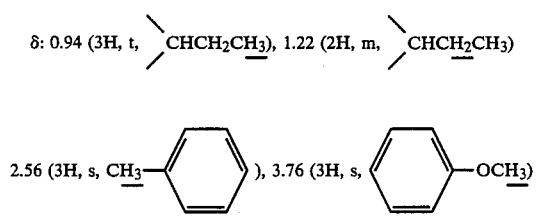

EXAMPLE 27

2-Hydroxy-5-{2-[2-(4-methoxyphenoxy)ethylamino]ethyl}benzenesulfonamide hydrochloride
Physicochemical properties
 Melting point: 237°–241° C. (decomposed)
 Elemental analysis for C$_{17}$H$_{22}$N$_2$O$_5$S.HCl

|            | C(%)  | H(%) | N(%) |
|------------|-------|------|------|
| Calculated: | 50.68 | 5.75 | 6.95 |
| Found:      | 50.45 | 5.64 | 6.99 |

Nuclear magnetic resonance spectra (CD$_3$OD) δ: 3.74 (3H, s, O—CH$_3$), 4.22 (2H, t, —CH$_2$—O)

EXAMPLE 28

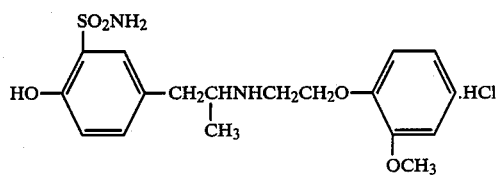

2-Hydroxy-5-{2-[2-(2-methoxyphenoxy)ethylamino]-2-methylethyl}benzenesulfonamide hydrochloride
Physicochemical properties
 Melting point: 211°–214° C.
 Elemental analysis for C$_{18}$H$_{24}$N$_2$O$_5$S.HCl

|            | C(%)  | H(%) | N(%) |
|------------|-------|------|------|
| Calculated: | 51.86 | 6.04 | 6.72 |
| Found:      | 51.72 | 6.00 | 6.59 |

Nuclear magnetic resonance (CD$_3$OD)
 δ: 1.28

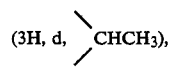

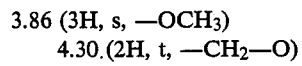

3.86 (3H, s, —OCH$_3$)
 4.30 (2H, t, —CH$_2$—O)

EXAMPLE 29

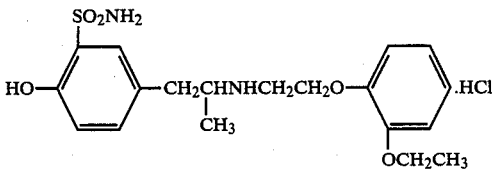

5-{2-[2-(2-Ethoxyphenoxy)ethylamino]-2-methylethyl}-2-hydroxybenzenesulfonamide hydrochloride
Physicochemical properties
 Melting point: 172°–173° C.
 Elemental analysis for C$_{19}$H$_{26}$N$_2$O$_5$S.HCl

|            | C(%)  | H(%) | N(%) |
|------------|-------|------|------|
| Calculated: | 52.96 | 6.31 | 6.50 |
| Found:      | 52.83 | 6.65 | 6.12 |

Nuclear magnetic resonance spectra (CD$_3$OD)
 1.26

(3H, d, \CHCH₃), 1.36 (3H, t, —CH₂CH₃)

4.10 (2H, q, —CH₂CH₃), 4.26 (2H, t, —CH₂C-H₂—O)

The starting materials and the reaction types applied to prepare the products of the above Examples 2, 3, 5 and 11-29 are shown below schematically;

Example No.

Starting Material & Reaction Type

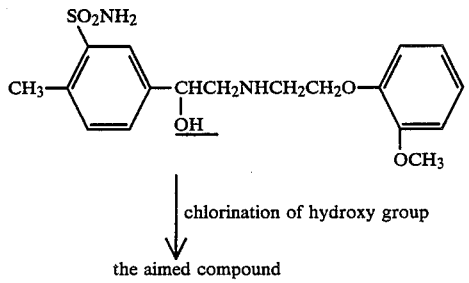

chlorination of hydroxy group the aimed compound

-continued

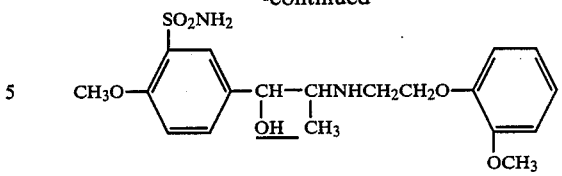

chlorination of hydroxy group the aimed compound

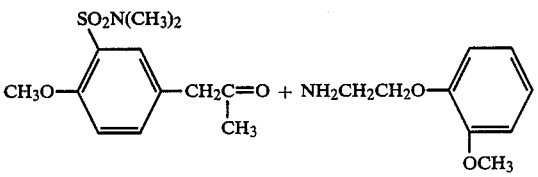

condensation tha aimed compound

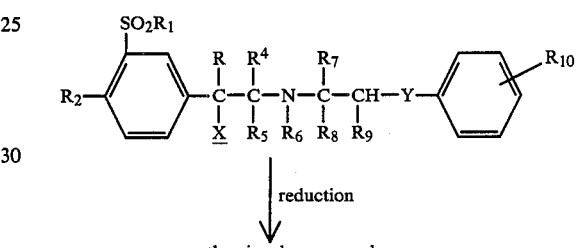

reduction the aimed compound
(X represents halogen; R, R₁, R₂ and R₄–R₁₀ in the formula represent the same group as the corresponding group of the aimed compound)

What is claimed is:

1. A method of producing alpha-adrenergic antagonistic action in a host which comprises administering to said host an alpha-adrenergic antagonistic amount of a pharmaceutical composition comprised of 5-{2-[2-(2-ethoxyphenoxy)ethylamino]-2-methylethyl}-2-methoxybenzenesulfonamide hydrochloride and a pharmaceutically acceptable excipient.

* * * * *